(12) United States Patent
van den Brink et al.

(10) Patent No.: US 7,375,807 B2
(45) Date of Patent: May 20, 2008

(54) SYSTEM FOR THE PREPARATION OF MULTIPLE SOLID STATE SAMPLES, IN PARTICULAR FOR SPECTROSCOPIC AND MICROSCOPIC ANALYSIS

(75) Inventors: Peter John van den Brink, Driebergen-Rijsenburg (NL); André Harmen Sijpkes, Almere (NL)

(73) Assignee: Avantium International B.V., Amsterdam (NL)

( * ) Notice: Subject to any disclaimer, the term of this patent is extended or adjusted under 35 U.S.C. 154(b) by 201 days.

(21) Appl. No.: 10/521,081

(22) PCT Filed: Jul. 15, 2002

(86) PCT No.: PCT/NL02/00472

§ 371 (c)(1),
(2), (4) Date: Sep. 15, 2005

(87) PCT Pub. No.: WO2004/008108

PCT Pub. Date: Jan. 22, 2004

(65) Prior Publication Data

US 2006/0098192 A1   May 11, 2006

(51) Int. Cl.
*G01N 1/10* (2006.01)
*B01L 3/00* (2006.01)
(52) U.S. Cl. ............... 356/246; 356/244; 422/99; 422/102
(58) Field of Classification Search ........... 356/244, 356/246; 422/98–102; 219/428, 385; 435/288.4, 435/305.2; 204/299 R, 180.1
See application file for complete search history.

(56) References Cited

U.S. PATENT DOCUMENTS

| | | | |
|---|---|---|---|
| 1,822,172 A | | 9/1931 | Pfleumer et al. |
| 2,887,946 A | | 5/1959 | Barnes et al. |
| 3,175,521 A | | 3/1965 | Hershberg |
| 3,795,467 A | | 3/1974 | Wheeler |
| 5,356,525 A | * | 10/1994 | Goodale et al. ............ 204/602 |
| 5,537,202 A | | 7/1996 | Komatsu et al. |
| 5,675,410 A | | 10/1997 | Kanda |
| 5,741,463 A | * | 4/1998 | Sanadi ....................... 422/101 |
| 5,772,967 A | * | 6/1998 | Wannlund et al. .......... 422/102 |
| 6,783,732 B2 | * | 8/2004 | Madden et al. ............... 422/63 |
| 6,830,732 B1 | * | 12/2004 | Hoffman et al. ............ 422/101 |
| 6,896,848 B1 | * | 5/2005 | Warhurst et al. ............. 422/99 |
| 6,939,516 B2 | * | 9/2005 | Hall et al. .................. 422/102 |
| 7,019,267 B2 | * | 3/2006 | Weinfield et al. ........... 219/428 |

* cited by examiner

*Primary Examiner*—Sang H. Nguyen
(74) *Attorney, Agent, or Firm*—Hoffmann & Baron, LLP

(57) ABSTRACT

A system for the preparation and handling of multiple solid state samples, in particular for spectroscopic and microscopic analysis. The system comprises a sample holder assembly for multiple solid-state samples. The sample holder assembly comprises a sample holding body having first and second sides (3a, 4a), provided with multiple sample receiving open-ended bores (5) extending through said body between said first and second sides, each bore (5) having a first opening at the first side and a second opening at the second side. Furthermore a closure body (10) is provided adapted to be mounted against the second side of the sample holding body, said closure body (10) having a closure side adapted to rest against the second side of the sample holding body for closing off the second openings of the bores (5) in said sample holding body. Compacting (23) means are provided for compacting samples filled in bores (5) of the sample holding body as these bores are closed off on the second side by the closure body.

22 Claims, 2 Drawing Sheets

SYSTEM FOR THE PREPARATION OF MULTIPLE SOLID STATE SAMPLES, IN PARTICULAR FOR SPECTROSCOPIC AND MICROSCOPIC ANALYSIS

CROSS-REFERENCE TO RELATED APPLICATIONS

This application is the National Stage of International Application No. PCT/NL02/00472, filed Jul. 15, 2002, the contents of which is incorporated by reference herein.

FIELD OF THE INVENTION

The present invention relates to a system for the preparation and handling of multiple solid state samples, in particular for spectroscopic and microscopic analysis.

BACKGROUND

In U.S. Pat. No. 5,675,410 a sample holder for a single sample is disclosed. This sample holder has an open ended bore with a first and second opening, the bore being delimited by an annular wall.

In order to prepare a sample the sample holder is placed on a closure body, thereby closing of the second opening of the bore.

The material to be sampled is introduced in the bore and then compacted using a compacting means. Once the sample is prepared the sample holder is placed in an analyser, in particular a spectroscopic analyser.

The known system is ineffective in case a large number of samples are to be analysed.

OBJECT OF THE INVENTION

The object of the present invention is to provide an improved sample preparation system for the preparation of a multitude of solid samples, in particular for spectroscopic or microscopic analysis.

SUMMARY OF THE INVENTION

The present invention achieves this object by a system for the preparation and handling of multiple solid-state samples, in particular for spectroscopic and microscopic analysis. This system comprises a sample holder assembly for multiple solid-state samples.

The sample holder assembly comprises a sample holding body having first and second sides, provided with multiple sample receiving open-ended bores extending through said body between said first and second sides, each bore having a first opening at the first side and a second opening at the second side.

A closure body is provided and is adapted to be mounted against the second side of the sample holding body, said closure body having a closure side adapted to rest against the second side of the sample holding body for closing off the second openings of the bores in said sample holding body.

The system further comprises compacting means for compacting samples filled in bores of the sample holding body as these bores are closed off on the second side by the closure body.

This new system is advantageous at the stage of preparation of the samples, as many samples can be prepared quickly. Another advantage is that all the samples are held in a common sample holding body, so that the samples can be analysed quickly without the need to remove a sample holder and replace it for another. Also the focussing or similar adaptation of the spectroscopic or microscopic analyser on a new sample takes less time than if separate sample holders are used, in particular if the surface of the samples all lie accurately in a single plane.

Another advantage of this system is the fact that it allows the preparation of a multitude of sample surfaces for analysis, and also enables preservation of that surface during storage and transport.

The invention further relates to a sample holding assembly.

Preferred embodiments of the system and sample holder assembly according to the invention are described in the claims and the following description referring to the drawings.

The present invention also relates to a method for the preparation of multiple samples and the spectroscopic and microscopic analysis of multiple samples using the system described herein.

The present invention also relates to the use of a sample holder assembly as described in a spectroscopic or microscopic analyser.

The system according to the invention is suitable in particular for spectroscopic and microscopic techniques such as reflective characterisation methods:

XPS or X-ray photoelectron spectroscopy,
XRD or X-ray diffraction,
Auger electron spectroscopy,
SIMS or secondary ion mass spectroscopy,
DRIFT or Diffusive reflection infrared Fourrier-transform spectroscopy,
SEM or Scanning electron microscopy,
EELS or Electron energy loss spectroscopy,
Raman scattering,
RAIRS or reflection absorption infrared spectroscopy,
IRES or infrared emission spectroscopy,
RBS or Rutherford Backscattering spectroscopy,
LEIS or low energy ion scattering,
STM Scanning tunneling microscopy,
AFM Atomic force microscopy, as well as transmissive characterisation methods:

Mössbauer spectroscopy,
EXAFS or X-ray absorption fine structure spectroscopy,
Transmission infrared spectroscopy.

It will be apparent that the methods referred to above are merely examples of suitable techniques.

DETAILED DESCRIPTION OF PREFERRED EMBODIMENTS

Figure 2:
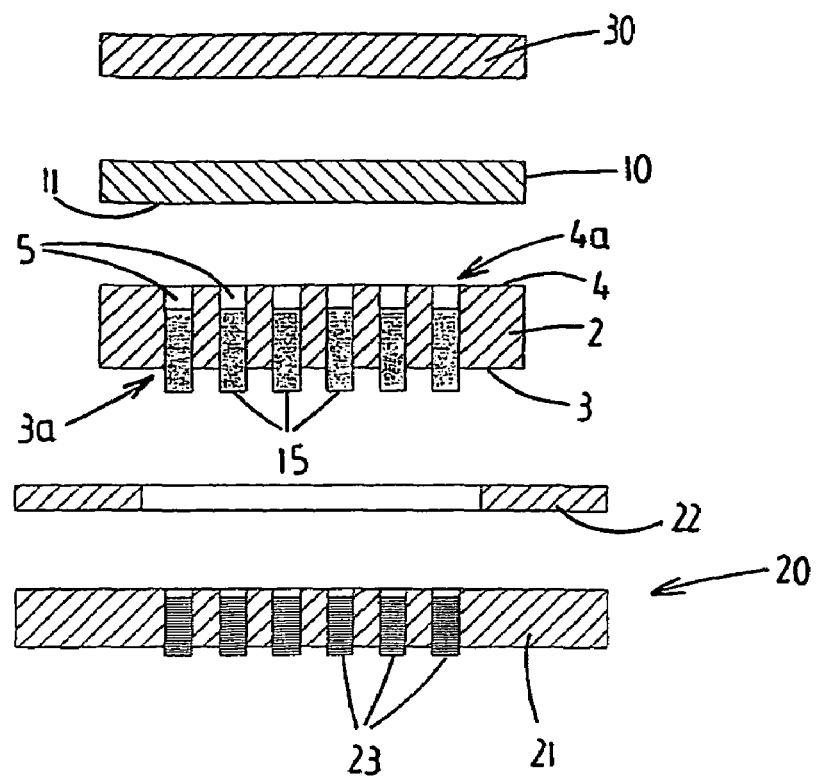
FIG. 2 shows the parts of the system of FIG. 1 in disassembled state.

An example of a system for preparing and handling multiple solid state samples, in particular for spectroscopic analysis, according to the invention will now be described referring to the FIGS. 1-3.

The system comprises a multiple sample holder assembly 1 for solid-state samples. This sample holder assembly 1 is assembled from a number of parts including a sample holding body 2 having a first side 3 and a second side 4, provided with an array of multiple sample receiving open-ended bores 5 extending through said body 2 between said first side 3 and second side 4.

Each bore 5 has a first opening 3a at the first side 3 and a second opening 4a at the second side 4.

The bores 5 are arranged here in a pattern of parallel rows and columns, however other patterns are also possible.

In a practical embodiment the sample holder body 2 is formed from a solid block, e.g. a metal block, wherein the bores 5 have been machined using suitable tooling.

The assembly 1 further comprises a closure body 10 adapted to be mounted against the second side 4 of the sample holding body 2.

The closure body 10 has a closure side 11 adapted to rest against the second side 4 of the sample holding body 2 for closing off the second openings 4a of the bores 5 in said sample holding body 2.

The system further comprises compaction and support plugs 15, which are each adapted to be fitted in a bore 5 via the first opening 3a. In the embodiment shown here a plug 15 slides smoothly inside the corresponding bore 5. In this embodiment the plugs 15 are preferably made from a hard material, preferably having a minimum tensile strength of 10 MPa, more preferably 50 MPa, most preferably 100 MPa.

Figure 1:
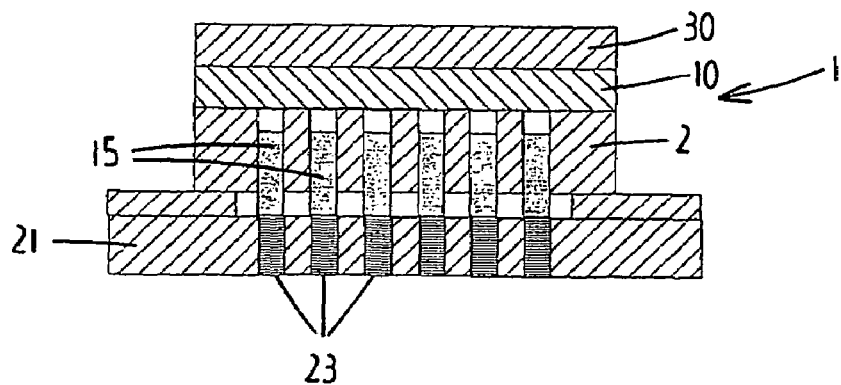
FIG. 1 shows an example of a system according to the invention in cross-section.
Figure 3:
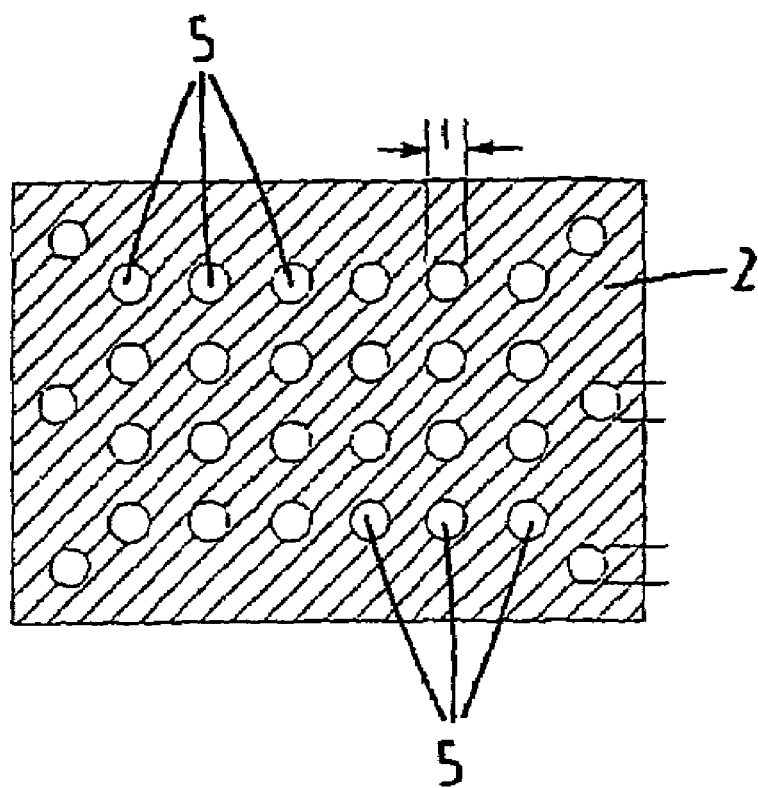
FIG. 3 shows a plan view of the sample holder body of FIGS. 1 and 2.

The system shown in FIGS. 1-3 further comprises a compacting device 20 adapted for pushing each of the plugs 15 into the bore 5 thereby compacting the sample. The compacting device 20 comprise a support 21 removably fixed over the first side of the sample holding body 2 with the interposition of a spacer 22.

The support 21 has screw threaded holes aligned with the bores 5 and provided with screws 23 for pushing the plugs 15 into the bores 5, thereby compacting the samples.

The second side 4a of the sample holder body 2 has a planar surface and the corresponding face of the closure body 10 also has a planar surface 11. Preferably the planar surface 11 of the closure body 10 is a mirror-finished or mirror quality surface, so as to obtain a very high quality surface of the samples at the second side 4a of the sample holder body 2.

For instance the planar surface 11 of the closure body 10 is polished.

Preferably the planar surface 11 of the closure body 10 is hard to avoid any deformation of the surface and to avoid any contamination of the material of the closure body onto the sample surfaces. Preferably the hardness of this planar surface is greater than 6 Mohs, more preferably greater than 7 Mohs and most preferably greater than 8 Mohs in order to prevent scratching of the planar surface 11.

It is envisaged that the planar surface 11 of the closure body 10 is one of the following materials: glass, ceramic, aluminumoxide, silicon, siliconcarbide, titaniumnitride, although other materials having a suitable hardness are also possible.

In the embodiment shown in FIGS. 1-3 an additional support body 30 is fitted to cover the outside of the closure body 10, which prevents overloading and/or distortion of the closure body 10, e.g. as the closure body is made of glass.

In order to prepare the samples using a system according to the embodiment shown in FIGS. 1-3 the support body 30, closure body 10 and sample holder body 2 are assembled, e.g. using bolts connecting the sample holder body 2 to the support body 30 clamping the closure body 10 there between.

Then the samples are introduced into bores 5 through the first openings 3a of the sample holder body 2.

The samples may for instance be introduced in the form of a powder (fine or coarse). The samples may also be introduced in the form of a slurry or paste, which then may be dried wholly or partly after introduced into the sample receiving bores 5.

In a possible embodiment the powder is grinded before introduction into the sample receiving bores, e.g. to a grain size of less than 0.5 millimetres.

Then the plugs 15 are introduced into the bores 5 in order to compact the samples between the stern face of the plugs 15 and the closure body 10. Preferably provision is made for air escape passages in order to allow the escape of air from the space beneath a plug 15. In practice this can be done for example by a suitable small play between the plug 15 and the wall of the bore 5, for example by selecting a slightly smaller space diameter plug than that of the bore 5.

After insertion of the plugs 15 the support 20 is fitted and the screws 23 are thigtened to push the plugs 15 into the bores 5.

In practice compacting could be done with pressures above 1 kg/cm2, preferably above 10 kg/cm2.

The compacting device can be adapted for sequentially compacting the samples of the simultaneous compacting of more than one or all of the samples.

After suitable compaction of the samples the sample holder assembly in its closed state can be transferred to a spectroscopic or microscopic analyser and mounted therein, for instance on a sample handling device Then the support plate 30 and the closure body 10 are removed in order to expose the faces of the samples at the side of the planar surface 4a. The samples can then be subjected to e.g. a reflective spectroscopic analysis, whereby the samples are still supported by the plugs 15.

A major advantage is that the exposed surfaces of the samples all lie accurately in a single plane 4a, which allows the spectroscopic or microscopic analyser to analyse each sample without the need to (totally) refocusing every time a new sample has to be analysed. This greatly reduces the time required for analysis of multiple samples in comparison to know single sample holders.

The sample holder assembly also allows for the parallel analysis of all or multiple samples in the sample holder.

Also the sample holder assembly does allow the samples to be treated physically or chemically prior to the spectroscopic or microscopic analysis. For instance, the samples can be heat treated in a reducing or oxidizing atmosphere to get them in the desired chemical or physical state. If the spectroscopic or microscopic technique and equipment allows this, these pretreatments can also be performed "in-situ". In this case the samples can be analysed during the pretreatment, or even under actual reaction conditions. Especially in the field of catalysis research and development this is highly desirable.

To enable treatment at elevated temperatures under various gas atmospheres extra means can be added to the sample holder assembly. Heating means may be connected externally or even integrated in the sample holder body. Means for the supply of gas can be attached as well. Also closure means may be used to guarantee exclusion of air and/or moisture from the environment after treatment during transport and/or storage of the samples. Those skilled in the art will understand the various measures to accommodate these extra means.

Figure 4:
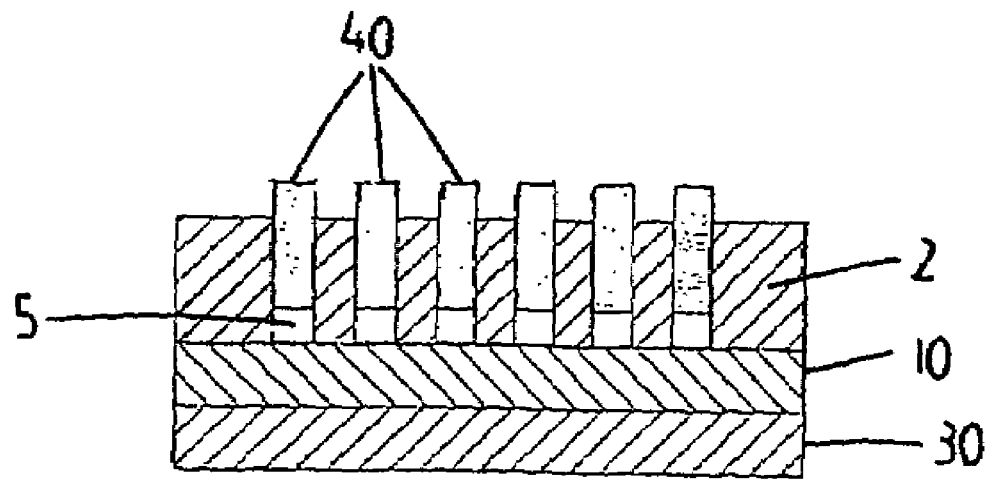
FIG. 4 shows a cross-section of an alternative sample holder assembly according to the invention.

In FIG. 4 a variant of the sample holding assembly of FIGS. 1-3 is shown. Parts corresponding to parts in FIG. 1-3 have the same reference numeral.

In this embodiment the plugs 40 are expandable in diameter under axial compression, either locally or over their entire length. Thereby the plugs 40 can be fixed in the bores 5 by expansion of the diameter. These plugs 40 are preferably made from a ductile material, preferably a metal, preferably having a maximum tensile strength of 400 Mpa, more preferably 350 Mpa, most preferably 300 Mpa.

It is conceivable that the samples in the bores 5 are compacted first using a compacting device in combination with compaction plugs. To do so the samples are filled in the bores 5 and then the compaction plugs are placed in the bores 5. By pressing these compaction plugs into the bores 5 further the samples are compacted. For instance the compaction device is a press (hydraulic, mechanical or simply a weight), a hammer (such as e.g. a pneumatic hammer). The compaction plugs can be integral with the compaction device or separate parts. After compaction these compaction plugs can be removed and then the support plugs 40 are put into place.

It is also conceivable that the compaction plugs remain in the bores 5 and that support plugs are placed in the bores behind the compaction plugs.

As an alternative means for securing plugs in the bores 5 an adhesive can be used.

In another variant the bores 5 are provided with screw thread (at least over a part thereof) and the plugs are also provided with screw thread, so that the plugs can be screwed into the bores 5 directly in order to compact the samples and also to hold the plugs in place. It will be clear that these screw plugs can also be used if compaction is done using other means and the plugs only serve to support the compacted samples.

It will be apparent that the compacting means for compacting samples filled in bores of the sample holding body can also be designed as means which are not to be fitted on the sample holder, e.g. as a (hydraulic) press for pushing each plug into the bore. Also other locking means could be provided to lock each plug in place after compaction of the sample.

It is also envisaged that the plugs are removed from the sample holder body before analysis of the samples. This is for instance relevant if the samples are to be subjected to a transmissive spectroscopic analysis. In particular when using this technique it can be advantageous that the thickness of the sample is measured, e.g. by measuring the position of the plug in the bore.

The bores 5 are shown to have a circular cross-section, however other cross-sections are possible as well.

Preferably the bores 5 have a diameter less than 2 cm, more preferably less than 1 cm, most preferably less than 0.5 cm, e.g. between 2 and 4 millimetres.

The system allows handling and transportation of the sample holder using a robot, which allows efficient loading of the samples into the sample receiving bores 5.

Also the sample holder does allow the samples to be subjected to other analysing techniques than spectroscopy, or even allows the samples first to be subjected to spectroscopy and then to another technique.

What is claimed is:

1. A system for the preparation and handling of multiple solid state samples for spectroscopic and microscopic analysis, said system comprising:
a sample holder assembly for multiple solid-state samples, said sample holder assembly comprising:
a sample holding body having first and second sides, provided with multiple sample receiving open-ended bores extending through said body between said first and second sides, each bore having a first opening at the first side and a second opening at the second side,
a closure body adapted to be mounted against the second side of the sample holding body, said closure body having a closure side adapted to rest against the second side of the sample holding body for closing off the second openings of the bores in said sample holding body,
compacting means for compacting samples filled in bores of the sample holding body as these bores are closed off on the second side by the closure body, and
plugs, each of the plugs adapted to be introduced into one of the bores via the first opening,
wherein the plugs are support plugs associated with said sample holding assembly, each support plug being adapted to be secured with respect to said bore for supporting a sample in said bore during at least one of the spectroscopic and microscopic analysis such that all exposed surfaces of the samples lie in a single plane.

2. System according to claim 1, wherein the plugs are also compaction plugs associated with said compaction means for compacting a sample in said bore.

3. System according to claim 1, wherein the plugs are compacting and support plugs for compacting a sample in said bore and also adapted to be secured with respect to said bore for supporting the compacted sample in said bore.

4. System according to claim 1, wherein the plugs are slideable in the bores and the compacting means are adapted for pushing the plugs into the bores thereby compacting the samples.

5. System according to claim 1, wherein the plugs are diametrically expandable under axial compression such that the plugs allow for expansion and thereby fixation in said bores.

6. System according to claim 1, wherein the plugs and the bores are screwthreaded.

7. System according to claim 1, wherein the system further comprises securing means for securing the plugs in the bores.

8. System according to claim 7, wherein the securing means comprise an adhesive.

9. System according claim 1, wherein the system wherein the compacting means comprise a support removably fixed over the first side of the sample holding body, said support having screwthreaded holes aligned with the bores and provided with screws for pushing the plugs into the bores.

10. System according to claim 9, wherein the planar surface of the closure body is a mirror-quality surface.

11. System according to claim 9, wherein the planar surface of the closure body is polished.

12. System according to claim 9, wherein the planar surface of the closure body is one of the following materials: glass, ceramic, aluminumoxide, silicon, siliconcarbide, titaniumnitride.

13. System according to claim 1, wherein the second side of the sample holder has a planar surface and wherein the corresponding face of the closure body also has a planar surface.

14. System according to claim 1, wherein the bores have a diameter less than 2 cm.

15. System according to claim 1, wherein the hardness of the closure side of the closure body is greater than 6 Mohs.

16. A method for preparing multiple samples for spectroscopic and microscopic analysis, comprising:
provided of a system for the preparation and handling of multiple solid state samples for spectroscopic and microscopic analysis, said system comprising a sample holder assembly for multiple solid-state samples, said sample holder assembly comprising:
a sample holding body having first and second sides, provided with multiple sample receiving open-ended bores extending through said body between said first and second sides, each bore having a first opening at the first side and a second opening at the second side,
a closure body adapted to be mounted against the second side of the sample holding body, said closure body having a closure side adapted to rest against the second side of the sample holding body for closing off the second openings of the bores in said sample holding body,
compacting means for compacting samples filled in bores of the sample holding body as these bores are closed off on the second side by the closure body,
plugs, each of the plugs adapted to be introduced into one of the bores via the first opening,
filing each sample into one of the a bores via the first opening thereof, said bores being closed at the second side by the closure body, and
compacting the samples using said compacting means, wherein the samples are supported by said support plugs such that during at least one of the spectroscopic and microscopic analysis all exposed surfaces of the samples lie in a single plane.

17. A method according to claim 16, wherein a thickness of the compacted samples is at least 100 micrometer.

18. A method according to claim 16, wherein a thickness of the sample is measured.

19. A method according to claim 16, wherein the closure body is removed from the second side of the sample holding body thereby exposing the corresponding surface of the samples, and then subjecting the samples to spectroseopic or microscopic analysis.

20. A method according to claim 19, wherein the samples are subjected to a physical or chemical treatment prior to or during the samples to spectroscopic or microscopic analysis.

21. A method according to claim 19, wherein the bores are open between the first opening and the sample so that also the surface of the samples directed towards the first side of the sample holder body are exposed, and subjecting the samples to a transmissive spectroscopic analysis.

22. A system for the preparation and handling of multiple solid state samples for spectroscopic and microscopic analysis, said system comprising:
a sample holder assembly for multiple solid-state samples, said sample holder assembly comprising:
a sample holding body having first and second sides, provided with multiple sample receiving open-ended bores extending through said body between said first and second sides, each bore having a first opening at the first side and a second opening at the second side,
a closure body adapted to be mounted against the second side of the sample holding body, said closure body having a closure side adapted to rest against the second side of the sample holding body for closing off the second openings of the bores in said sample holding body, and
compacting means for compacting samples filled in bores of the sample holding body as these bores are closed off on the second side by the closure body, and
plugs, each of the adapted to be introduced into one of the bores via the first openings, wherein the plugs are support plugs associated with said sample holding assembly, each support plug being adapted to be secured with respect to said bore for supporting a sample in said bore during at least one of the spectroscopic and the microscopic analysis such that all exposed surfaces of the samples lie in a single plane, and wherein the compacting means comprise a support removably fixed over the first side of the sample holding body, said support having screwthreaded holes fixed over the first side of the sample holding body and aligned with the bores and provided with screws for pushing the plugs into the bores, and wherein the second side of the sample holder has a planar surface and wherein the corresponding face of the closure body also has a planar surface, which planar surface is polished, is a mirror-quality surface, and is one of the following materials: glass, ceramic, aluminiumoxide, silicon, siliconcarbide, titaniumnitride.

* * * * *